United States Patent [19]

Donnet et al.

[11] Patent Number: 5,461,033
[45] Date of Patent: Oct. 24, 1995

[54] MODULATION OF CLASS II ANTIGEN EXPRESSION

[75] Inventors: Anne Donnet, Saint-Legier; Anthony C. Huggett, Lausanne; Eduardo Schiffrin, Crissier, all of Switzerland

[73] Assignee: Nestec S.A., Vevey, Switzerland

[21] Appl. No.: 391,634

[22] Filed: Feb. 21, 1995

Related U.S. Application Data

[63] Continuation of Ser. No. 907,056, Jul. 1, 1992, abandoned.

[30] Foreign Application Priority Data

Aug. 12, 1991 [EP] European Pat. Off. .............. 91810629

[51] Int. Cl.$^6$ .......................... C07K 14/495; A61K 38/18
[52] U.S. Cl. .................. 514/12; 514/2; 514/21; 530/351; 424/85.1
[58] Field of Search ................... 514/2, 12, 21; 530/351; 424/85.1

[56] References Cited

U.S. PATENT DOCUMENTS 4,440,860  4/1984  Klagsbrun ........................... 435/240.3

FOREIGN PATENT DOCUMENTS

| 0269408 | 6/1988 | European Pat. Off. . |
| 0313515 | 4/1989 | European Pat. Off. . |
| 9000900 | 2/1990 | WIPO . |
| 9003812 | 4/1990 | WIPO . |

OTHER PUBLICATIONS

Skulme "The Etiology, Pathenogenesis & Early Diagnosis of Cancer & Precancerous Diseases of The Stomach" pp. 148–149 1959.
Chemical Abstracts, vol. 107, No. 9, Aug. 31, 1987, No. 76199v.
Pediatric Research, El-Youssel, et al., vol. 25, No. 4, pp. 269A, 1989.
Immunology, Hughes, et al, "Expression of MHC class II (Ia) Antigen by the Neonatal Enterocyte: The effect of treatment with interferon–gamma." vol. 72, pp. 491–496, 1991.
European Journal of Biochemistry, Cox, D. T., et al., vol. 197, No. 2, pp. 353–358, Apr. 1991.
*Journal of Protein Chemistry*, Jin, Y., et al, vol. 10, No. 5, pp. 565–575, 1991.
Benacerraf, B., Role of MHC Gene Products in Immune Regulation, Science, 212, 1229 (1981).
Czarniecki, C. W., et al., Transforming Growth Factor–$\beta_1$ Modulates The Expression of Class IV Histocompatibility Antigens On Human Cells, J. Immunol., 140, 4217–4223 (1988).
Huggett, A. C. et al., Altered Responsiveness of Rat Liver Epithelial Cells To Transforming Growth Factor $\beta_1$ Following Their Transformation With V–raf, Cancer Res., 50, 7768–7775 (1990).
Kehrl, J. H. et al., Transforming Growth Factor $\beta$ Is An Important Immunomodulatory Protein for Human B Lymphocytes, J. Immunol., 137, 3855–3860 (1986).
Kehrl, J. H. et al., Production Of Transforming Growth Factor $\beta$ By Humman T Lymphocytes And Its Potential Role in The Regulation of T Cell Growth, J. Exp. Med., 163, 1037–Poso (1986).
Lebman D. A., et al., Mechanism For Transforming Growth Factor $\beta$ and IL–2 Enhancement of IgA Expression In Lipopolysaccharide–Stimulated B Cell Cultures, J. Immunol., 144, 952–959 (1990).
Mayer, L., et al., Evidence for Function Ia Molecules on Gut Epithelial Cells in Man, J. Exp. Med. 166, 1471–1483 (1987).
Mayer, L., et al. Expression of Class II Moleucles On Intestinal Epithelial Cells In Humans, Gastroenterology, 100, 3–12 (1991).
Quaroni, A. et al., Epithelial Cell Cultures From Rat Small Intestine, J. Cell, Biology, 80, 248 (1979).
Roberts, A. B., et al., The Transforming Growth Factor–$\beta$s, Peptide Growth Factors and Their Receptors, vol. 1, 419–472, eds. Sporn M. B., et al., Springer (1990).
Ristow, H. J., BSC–1 Growth Inhibitor/Type $\beta$ Transforming Growth Factor Is a Strong Inhibitor of Thymocyte Proliferation Proc Natl. Acd Sci USA, 83, 5531–5533, (1986).
Schlusener, H. J., Transforming Growth Factors Type $\beta_1$ and $\beta_2$ Suppress Rat Astrocyte Autoantigen Presentation and Antagonize Hyperinduction of Class II Major Histocompatibility Complex Antigen Expression By Interferon–$\gamma$ and Tumor Necrosis Factor $\alpha$, J. Neuroimmunol., 27, 41–47, (1990).
Smith, P. K., Measurement of Protein Using Bicinchoninic Acid, et al., Annl. Biochem, 150, 76–85, (1985).
Snook, J. A., et al., Serum and Tissue Autoantibodies To Colonic Epithelium In Ulcerative Colitis, Gut, 32, 163–166, (1991).
Stoeck, M., et al. Comparison of the Immunosuppressive Properties of Milk Growth Factor and Transforming Growth Factors $\beta$1 and $\beta$2, J. Immunol., 143, 3258–3265 (1989).
Stoeck, M. et al., Transforming Growth Factors $\beta$1 and $\beta$2 as Well As Milk Growth Factor Decrease Anti–DC3–Induced Proliferation of Human Lymphocytes Without Inhibiting the Anti–CD3–Mediated Increase of $[Ca^{2+}]_i$ and The Activation of Protein Kinase C, FEBS Lett., 249, 289 292 (1989).
West, D. W., The Origin, Transport and Function of Hormones and Growth Factors In Milk, Exp. Clin. Endocrinol, 8, 145–146 (1989).
Zuber P., et al; Transforming Growth Factor–$\beta$2 Down–Regulates HLA–DR Antigen Expression on Human Malignant Glioma Cells, Eur. J. Immunol 18, 1623–1626 (1988).
Zweibaum, A., et al., Enterocytic Differentiation of A Subpopulation of the Human Colon Tumor Cell Line HT–29 Selected For Growth In Sugar–Free Medium and its Inhibition By Glucose, J. Cell Physiol; 122, 21 (1985).
Challenges In IBD Research: Agenda for The 1990's, National Foundation for Ileitis and Colitis, Feb. 21, 1990, Washington, D.C.

*Primary Examiner*—Michael G. Wityshyn
*Assistant Examiner*—Nancy J. Degen
*Attorney, Agent, or Firm*—Vogt & O'Donnell

[57] ABSTRACT

The expression of Class II antigen expression by intestinal epithelial cells is modulated by administering to a mammal in need thereof an effective amount of TGF–$\beta$2.

4 Claims, No Drawings

MODULATION OF CLASS II ANTIGEN EXPRESSION

CROSS REFERENCE TO RELATED APPLICATION

This application is a continuation application of Ser. No. 07/907,056, filed Jul. 1, 1992, now abandoned.

FIELD OF THE INVENTION

This invention relates to the use of milk-derived polypeptides of the transforming growth factor beta family for the regulation of immune responses at the gut level associated with MHC (major histocompatibility complex).

This invention relates especially to the use of mammalian milk or colostrum derived TGF-β-like MGF (milk growth factor) for the preparation of a food composition, an enteral preparation or a pharmaceutical composition, as well as to a food composition or to an enteral preparation containing an effective amount of mammalian milk or colostrum derived TGF-β-like MGF.

DESCRIPTION OF THE PRIOR ART

Human and bovine milk contain many biologically active polypeptides including growth factors (West, D. W. Exp. Clin.Endocrinol. 8 145–146,1989). One of these factors, MGF (milk growth factor) was recently identified as identical to or having close homology to a member of the transforming growth factor beta (TGF-β) family, notably TGF-β2 (Cox D. A. et al. Eur. J. Biochem. 197 353–358, 1991). TGF-β is the general name for a family of polypeptides consisting of at least 5 distinct but closely related members, which have considerable structural and biological homologies (Roberts, A. B., et al. In: Peptide Growth Factors and their Receptors Vol. 1, pp. 419–472, Eds. Sporn M. B. et al., Springer, 1990). TGF-βs are homodimeric proteins of about 25 kDa consisting of identical 12.5 kDa polypeptide chains linked through disulphide bridges. They may form latent complexes with other proteins and these complexes may be activated by acid treatment or mild proteolysis (Roberts, A. B. et al.). They are multipotent, having a number of biological activities depending upon the target cell type, its state of differentiation and the presence of other factors. These activities include stimulation or inhibition of cell proliferation and differentiation, regulation of extracellular matrix deposition, immunomodulation, steroidogenesis and angiogenesis (Roberts, A. B. et al.).

Expression of MHC-Class II on the surface of antigen-presenting cells is a prerequisite for the presentation of exogenous antigen to T-cells (Benacerraf, B., Science 212 1229, 1981). Epithelial cells in the intestinal villus of the adult rodent constitutively express MHC-Class II while its expression by crypt cells depends in part on their spatial location in the intestine (Hughes, A., et al. Immunol. 72 491, 1991). In the postpartum period in the rodent there is little or no expression of MHC-Class II by enterocytes until after weaning, thus indicating the presence of a suppressive factor in milk (Hughes, A. et al.).

TGF-βs, including TGF-β2, have a number of immunoregulatory properties and act at several stages of the inflammatory and immune reaction. For example they inhibit the proliferation of T and B lymphocytes (Kerhl, J. H., et al. J.Immunol. 137:3855–3860, 1986; Kerhl, J. H., et al. J.Exp.Med. 163:1037–1050, 1986) and thymocytes (Ristow, H. J. Proc. Natl. Acad. Sci. USA 83 5531–5534,1986). They also antagonize the effects of interleukins including IL-1, IL-2 and IL-3 and other immunoregulatory agents such as tumor necrosis factor and interferons (Roberts, A. B. et al.). Although most of their effects on immune cells are inhibitory, TGF-βs appear to play a critical role in isotype switching of IgG and IgM secreting cells to IgA secreting cells (Lebman, D. A., et al. J.Immunol. 144:952–959, 1990). With particular reference to reported immunosuppressive effects of MGF, this factor has been shown to decrease the proliferation of human lymphocytes induced by anti-CD3 or interleukins (Stoeck, M., et al. FEBS Lett. 249 289–292, 1989); Stoeck, M., et al. J.Immunol. 143 3258–3265, 1989). TGF-βs interfere with certain accessory cell functions important in antigen presentation and specifically were shown to suppress MHC-Class II expression by melanomas, glial cells and astrocytes (Czarniecki, C. W., et al J.Immunol. 140 4217–4223, 1988; Schlusener H. J. J.Neuroimmunol. 24 41–47, 1990; Zuber, P. et al. Eur. J.Immunol. 18 1623–1626,1988). However, the regulation of MHC-Class II expression on epithelial cells in the intestine by TGF-βs or MGF has not hitherto been reported.

Altered regulation of MHC-Class II has been implicated in several gastrointestinal disorders. The presence of active inflammation at the gut level generally results in an increase in MHC-Class II expression on human intestinal epithelium and lamina propria (Mayer, L., et al. Gastroenterology 100 3–12, 1991). This increase is a conspicuous component of Inflammatory Bowel Disease (IBD), (Mayer, L. et al.). In IBD, tissue damage is due either to an autoimmune attack on the cellular components of the host intestinal mucosa (Snook, J. A., et al. Gut 32 163–166, 1991), or to a disorder in the mucosal immune regulation with an over-reactivity to luminal antigens in the gut, based on a defective down-regulation of this response (Challenges in IBD Research: Agenda for the 1990's. National Foundation for Ileitis and Colitis. Feb. 21, 1990. Washington D.C.). Both possibilities imply the existence of a disregulation of the mucosal immune response and emphasize an immunologic role in the initiation and perpetuation of the inflammatory response.

SUMMARY OF THE INVENTION

The object of the present invention is to provide a food composition, an enteral preparation or a pharmaceutical preparation for regulating MHC mediated immune responses in the mammalian gastrointestinal tract, and more especially for the treatment of Inflammatory Bowel Diseases (e.g. Crohn's disease, Ulcerative Colitis) or Graft-vs-Host reactions in humans or animals, for the prevention of diarrhea in weaning humans or animals, or for the prevention of allergic reactions in the gastrointestinal tract in humans or animals.

Thus, in accordance with the method of the invention, the expression of Class II antigen by intestinal epithelial cells is modulated by administering to a mammal in need thereof an effective amount of TGF-β2.

The food composition, the enteral preparation, and/or the pharmaceutical preparation according to the present invention contain an effective amount of mammalian milk or colostrum derived TGF-β2-like MGF for the modulation of MHC expression in the gastrointestinal tract of humans or animals; said amount being preferably effective for the treatment of Inflammatory Bowel Diseases (e.g. Crohn's disease, Ulcerative Colitis) or Graft-vs-Host reactions in humans or animals, for the prevention of diarrhea in weaning humans or animals, or for the prevention of allergic reactions in the gastrointestinal tract in humans or animals.

DETAILED DESCRIPTION OF THE INVENTION

For preparing the food composition or the enteral preparation, or for carrying out the uses according to the present invention, a bioactive milk component, identical to or with close homology to TGF-β2 may be prepared in an enriched form from mammalian milk products, especially from bovine milk products, e.g. as disclosed in European Patent Application Publication No. 313 515 A1 (CIBA-GEIGY AG) p. 6 1. 11 to p. 7 1. 34 and Examples 1 to 3, and having TGF-β2-like activity on the proliferation of mammalian liver epithelial cells and on the expression of MHC by mammalian intestinal epithelial cells. Henceforth this bioactive milk factor is termed TGF-β2-like MGF.

Test 1, TGF-βs in Milks

Normal rat liver epithelial (RLE) cells which have previously been shown to be sensitive to the growth inhibitory effects of TGF-βs (Huggett, A. C., et al. Cancer Res. 50 7468–7475, 1990) were incorporated into a bioassay for the analysis of TGF-βs in milks and in acid-treated milk fractions and milk powders. Measurement of inhibition of DNA synthesis by $^3$H-Thymidine incorporation was performed as described previously (Huggett A. C. et al.). Antibodies raised against TGF-βs (British Bio-technology Ltd.) were coincubated with standards or samples prior to bioassay analysis in order to determine inhibitory activity specific to TGF-β isoforms. Using this assay a 50% inhibition of RLE cell DNA synthesis is obtained with 50 pg/ml of TGF-β1 or TGF-β2.

Human and bovine milk were delipidated by centrifugation, desalted on PD-10 columns (Pharmacia) eluted with PBS and then sterilized by filtration through 0.2 μm membranes (Millipore). Protein contents were monitored using the method of Smith et al (Smith P. K., et al. Anal. Biochem. 150: 76–85, 1985). For analysis of latent acid-activatable TGF-βs, the milk samples were adjusted to pH 4 with 1N HCl, centrifuged at 40000 g for 60 min to separate whey and casein fractions which were then neutralized with 1N NaOH and dialyzed against PBS. Dilutions were then analyzed using the RLE cell bioassay together with a series of TGF-β standard solutions. An estimation of the amount of TGF-β-like activity was determined by a comparison of the degree of inhibition of DNA synthesis obtained with the samples against TGF-β standard curves. The identification of specific isoforms of TGF-β was determined by examining the effects of isoform-specific neutralizing antibodies on the inhibitory activity.

This test demonstrates that both human and cows milk contain acid-activatable TGF-β2-like MGF which is mainly associated with the casein fraction (Table 1).

TABLE 1

TGF-β2-like MGF activity in Milks

| Sample | Active TGF-β2-like MGF (μg/g protein) |
| --- | --- |
| Bovine Milk | <0.01 |
| Bovine Acid Casein | 0.52 |
| Human Milk* | <0.2 |
| Human Acid Casein | 0.75 |

*This value is overestimated due to the large amounts of EGF in these samples which interfere with the assay.

Tests 2 and 3
Suppression of MHC-Class II Expression by Intestinal Epithelial Cells The HT-29 intestinal epithelial line derived from human colonic epithelial cells (Fogh, J. et al. In: Human Tumor Cells "in vitro". J. Fogh, ed. Plenum Publishing Corp., New York, pp. 115, 1975), were maintained in an undifferentiated state in glucose-containing media (Zweibaum, A., et al. J.Cell.Physiol., 122: 21, 1985). When the cells reached 70–80% confluence, they were exposed, over a 48 h period, to one of the following treatments: human recombinant interferon-gamma (IFN-γ, 100 U/ml) alone (Boehringer Mannheim); IFN-γ in combination with TGF-β2; IFN-γ followed by TGF-β2; TGF-β2 alone followed by IFN-γ; or, as a control, culture media alone. Cells were washed and retreated after the first 24 h. TGF-β2 was used at doses ranging from 0.05 ng to 4 ng per ml. Following the treatment period, the cells were washed, fixed and the plates stored frozen at −20° C. until required.

The avidin-biotin complex method of immunoperoxidase staining (Cerf-Bensussan, N., et al. J.Immunol., 130: 2615, 1983) was performed on monolayers utilising the mouse monoclonal antibody L234 (Becton Dickinson), which recognises the human MHC-Class II histocompatibility antigen HLA-DR. Mouse myeloma IgG protein (Zymed) served as a control. In another series of experiments, a normal rat small intestinal cell line, IEC-18 (Quaroni, A., et al. J.Cell Biology, 80 248, 1979) was grown to 50% confluency and subjected to IFN-γ and/or TGF-β2 in the combinations listed above. Cells were then detached from the culture dishes using Versene (Life Technologies Ltd.) and stained, in suspension, using a standard, direct immunofluorescence technique. Briefly, cells were washed, incubated with normal serum for 5 min and then with the FITC-conjugated mouse monoclonal antibody MRC OX-6 (Serotec) which recognises the rat Class II MHC antigen. Cells were then washed and fixed for at least 1 h with 1% paraformaldehyde before analysis in the FACScan (Becton Dickinson).

During food allergy and inflammatory diseases, intestinal epithelial cells express high levels of Class II antigen thought to be mediated, at least in part, by inflammatory cytokines such as IFN-γ. The HT-29 undifferentiated cells employed in the assay described, do not constitutively express Class II molecules. To partially mimic events taking place during the onset of intestinal inflammation, the cells were exposed to IFN-γ. The effect of TGF-β2 on this reaction was then examined. Exposure to IFN-γ induced Class II expression on the HT-29 cells but this effect was abrogated by pretreatment with TGF-β2 at all the doses tested (Table 2). In contrast, the other combinations of cytokines tested resulted in high levels of Class II expression. The majority of IEC-18 cells already expressed Class II molecules but showed increased expression following treatment with IFN-γ (Table 3). Once again, TGF-β2 suppressed this induction. Thus, at the onset of inflammatory intestinal reactions, TGF-β2 may modulate local expression of Class II antigens.

TABLE 2

Effect of TGF-β2 on MHC-Class II expression by human intestinal epithelial cells (HT-29).

| Treatment | | |
| --- | --- | --- |
| (0–24 h) | (24–48 h) | MHC-II Expression |
| none | none | − |
| none | IFN-γ | ++ |
| IFN- | none | ++ |

TABLE 2-continued

Effect of TGF-β2 on MHC-Class II expression by human intestinal epithelial cells (HT-29).

| Treatment | | MHC-II Expression |
|---|---|---|
| (0–24 h) | (24–48 h) | |
| IFN-γ | IFN-γ | +++ |
| TGF-β2 | none | − |
| TGF-β2 | TGF-β2 | − |
| TGF-β2 | IFN-γ | − |
| IFN-γ | TGF-β2 | ++ |
| TGF-β2 + IFN-γ | TGF-β2 + IFN-γ | ++ |

Staining: − negative
+ weak
++ strong
+++ very strong

TABLE 3

Effect of TGF-β2 on MHC-Class II expression by rat intestinal epithelial cells (IEC-18).

| Treatment | | MHC-II Expression |
|---|---|---|
| (0–24 h) | (24–48 h) | (% positive cells) |
| none | none | 73.6 ± 1.5 |
| none | IFN-γ | 85.3 ± 5.3 |
| IFN-γ | IFN-γ | 95.8 ± 0.6 |
| TGF-β2 | none | 67.3 ± 1.8 |
| TGF-β2 | IFN-γ | 75.8 ± 0.3 |
| TGF-β2 + IFN-γ | TGF-β2 + IFN-γ | 86.9 ± 1.5 |

The demonstration of MHC-Class II antigens on human and rodent intestinal cells supports the notion that these cells may act as antigen presenting cells (Mayer, L., et al. J.Exp. Med. 166 1471–1483, 1987). The epithelial cell the intestine has been considered a major participant in the etiopathogenesis of IBD. An increase in their expression of MHC-Class II could lead to an increased epithelial-T-helper lymphocyte interaction and this, in turn, could be a primary event in IBD or a perpetuating mechanism. The present studies demonstrate for the first time the action of TGF-β2 (and TGF-β2-like MGF) on suppression of MHC-Class II expression on intestinal epithelial cells. According to these findings, the availability of an immunosuppressive agent acting topically at the surface of the intestinal mucosa could provide a new tool to interrupt the pathogenic mechanism involved in IBD and other inflammatory-immune conditions in the gut, namely Coeliac Disease and Graft-vs-Host reactions.

Example 1

TGF-β2-like MGF prepared in enriched form from bovine milk as disclosed above is added to a nutritionally balanced enteral product comprising about 10% of dry matter in such a quantity that the enteral preparation thus obtained comprises an amount of about 0.1 to 50, preferably 0.5 to 20 μg of TGF-β2-like MGF per g of dry matter.

The enteral preparations prepared in this way are effective in suppressing MHC-Class II expression by intestinal epithelial cells.

Example 2

TGF-β2-like MGF prepared in enriched form from bovine milk as disclosed above is added to a balanced food product in liquid or powder form in such a quantity that the food composition thus obtained comprises an amount of about 0.1 to 50, preferably 0.5 t0 20 μg of TGF-β2-like MGF per g of dry matter.

The food composition prepared in this way are effective in suppressing MHC-Class II expression by intestinal epithelial cells.

We claim
1. A method of treating Crohn's disease comprising administering to a human an effective amount of a nutritionally balanced enteral product comprising a TGF-β2-containing acid casein fraction isolated from bovine milk, wherein the enteral product contains from about 0.1 to 20 μg TGF-β2 per gram of dry matter.

2. A method according to claim 1 wherein the enteral product has a dry matter content of about 10% by weight.

3. A method according to claim 1 wherein the enteral product contains from about 0.1 to 0.5 μg TGF-β2 per gram of dry matter.

4. A method according to claim 3 wherein the enteral product has a dry matter content of about 10% by weight.

* * * * *